(12) United States Patent
Hou et al.

(10) Patent No.: US 11,674,152 B2
(45) Date of Patent: Jun. 13, 2023

(54) ANTI-ARMYWORM USE OF CRY1AB/CRY1ACZM GENE

(71) Applicant: CHINA NATIONAL SEED GROUP CORPORATION, LTD., Beijing (CN)

(72) Inventors: Xianbin Hou, Beijing (CN); Rongjian Ye, Beijing (CN); Qiuming She, Beijing (CN); Yu Han, Beijing (CN); Zhiguo Han, Beijing (CN); Qiao Yang, Beijing (CN); Wei Huang, Beijing (CN); Qianqian Yang, Beijing (CN); Yanlin Hu, Beijing (CN); Jicui An, Beijing (CN); Yingli Wang, Beijing (CN); Yazhou Yang, Beijing (CN); Junqing Zhou, Beijing (CN); Wanggen Zhang, Beijing (CN)

( * ) Notice: Subject to any disclaimer, the term of this patent is extended or adjusted under 35 U.S.C. 154(b) by 27 days.

(21) Appl. No.: 16/968,850

(22) PCT Filed: Feb. 2, 2019

(86) PCT No.: PCT/CN2019/074612
§ 371 (c)(1),
(2) Date: Aug. 10, 2020

(87) PCT Pub. No.: WO2019/154374
PCT Pub. Date: Aug. 15, 2019

(65) Prior Publication Data
US 2021/0017536 A1    Jan. 21, 2021

(30) Foreign Application Priority Data

Feb. 11, 2018 (CN) .......................... 201810140845.9

(51) Int. Cl.
*C12N 15/82* (2006.01)
*C07K 14/32* (2006.01)
*C07K 14/325* (2006.01)

(52) U.S. Cl.
CPC ........ *C12N 15/8286* (2013.01); *C07K 14/325* (2013.01)

(58) Field of Classification Search
CPC .......................... C12N 15/8286; C07K 14/325
See application file for complete search history.

(56) References Cited

U.S. PATENT DOCUMENTS

2018/0362998 A1*  12/2018  Liu ........................ C12N 15/62

FOREIGN PATENT DOCUMENTS

| CN | 103688974 A | 4/2014 | |
|----|-------------|--------|---|
| CN | 104744575 A | 7/2015 | |
| CN | 104861074 A | 8/2015 | |
| CN | 106497966 A * | 3/2017 | |
| CN | 106701789 A | 5/2017 | |
| WO | WO 2015/067194 A1 | 5/2015 | |
| WO | WO-2017012577 A1 * | 1/2017 | ............. C12N 15/62 |

OTHER PUBLICATIONS

ISA/CN; International Search Report of PCT/CN2019/074612, dated May 9, 2019; 3 pgs.
SuJuan Yang; Screening and analysis of Bt protein with insect resistance to oriental armyworm and Asian corn borer; Chinese Doctoral Dissertations & Master's Theses Full-text Database (Master), Agriculture Science and Technology; D046-106; Apr. 15, 2016; 12 pages.
China National Intellectual Property Administration; Office Action in Application No. 201810140845.9; dated Nov. 2, 2021; 5 pages.

* cited by examiner

*Primary Examiner* — Charles Logsdon
*Assistant Examiner* — Wayne Zhong
(74) *Attorney, Agent, or Firm* — Kilpatrick Townsend & Stockton LLP (57) ABSTRACT

Provided is a novel anti-armyworm use of cry1Ab/cry1AcZM gene. Said gene can be used for controlling or killing Mythimna separate (Walker) and reducing injury to plants by Mythimna separate.

9 Claims, 1 Drawing Sheet
Specification includes a Sequence Listing.

ANTI-ARMYWORM USE OF CRY1AB/CRY1ACZM GENE

CROSS-REFERENCE TO RELATED APPLICATIONS

The present application is a § 371 National Phase Application of PCT/CN2019/074612, filed Feb. 2, 2019, which application claims the priority under Article 8 of the PCT to Chinese Patent Application No. 201810140845.9, filed on Feb. 11, 2018, the entire contents of which are incorporated herein by reference in their entireties for all purposes herein.

SEQUENCE LISTING

The instant application contains a Sequence Listing which has been submitted electronically in ASCII format and is hereby incorporated by reference in its entirety. Said ASCII copy, created on Aug. 10, 2020, is named 18C83755US-Sequence-Listing3-Updated.txt and is 2,857 bytes in size.

TECHNICAL FIELD

The present application relates to the field of plant biotechnology, and more particularly, to novel anti-armyworm use of cry1Ab/cry1AcZM gene.

BACKGROUND

The insecticidal protein of *Bacillus thuringiensis* (Bt) has specific toxicity to insects such as Lepidoptera, Coleoptera and Diptera and invertebrates.

However, the toxicity of the same Bt insecticidal protein to different pests of Lepidoptera was significantly different. For example, transgenic cottons have been planted in large areas in China for many years, and mainly contain Cry1Ac insecticidal protein, which has a strong toxic effect on *Helicoverpa armigera* and effectively controls the injury caused by *Helicoverpa armigera*; However, the insecticidal protein does not have a lethal effect on *Spodoptera exigua* of the Lepidoptera, so that the secondary pests *Spodoptera exigua* become the major pests and affect cotton yield (Chen Ruirui. Mechanism of sensitivity differences between *Spodoptera exigua* and *Helicoverpa armigera* to Cry1Ca and Cry1Ac, a Master's thesis, Nanjing Agricultural University, 2012).

A number of studies have shown that Bt insecticidal proteins have toxic effects on armyworms and that the toxic effects vary in different Bt insecticidal proteins. The differences are mainly due to the target armyworm species and the different degrees of killing the same target armyworm. Williams et al. reported that a maize hybrid with a transgenic Bt insecticidal protein planted in the southern of the United States showed high resistance to *Spodoptera frugiperda*; In 1999, R. E. lynch et al. used 8 hybrids of sweet corns with transgenic Bt insecticidal protein indoors to feed 3-day and 6-day *Spodoptera frugiperda*, of which the leaves and stems of 7 hybrids were highly resistant to *Spodoptera frugiperda* (Yang Chunying et al. Advances in Transgenic Maize with Bt Virus Protein and Its Insect Resistance. Corn Science, 2001, 9:88-93). The biological activity of Mythimna separate (Walker) was determined by artificial feeding of different Bt insecticidal proteins. The results showed that Cry1Ac, Cry1Ab, Cry2Ab, Cry1Be and Cry1Bb proteins had insecticidal activity; Cry9Aa, Cry9Eb and Cry9Ee proteins had inhibitory effects on the growth of Mythimna separate (Walker); Cry1Ba and Cry1Ca had no significant activity (Yang Sujuan et al., Screening and Analysis of Bt Protein with Insecticidal Activity against armyworm. Plant protection, 2016, 42: 30-35). MON810, transgenic maize developed by Monsanto, USA, has an effect on the density of *Spodoptera frugiperda* at 2-age, 4-age, and 6-age stage (Chilcutt, C. F., et al., 2007. Effects of *Bacillus thuringiensis* transgenic corn on corn earworm and fall armyworm (Lepidoptera: Noctuidae) densities. *J Econ. Entomol.* 100: 327-334), can reduce the injury caused by *Spodoptera frugiperda* pests (Buntin G D., et al., Evaluation of yieldgard transgenic resistance for control of fall armyworm and corn earworm (Lepidoptera: Noctuidae) on Corn. Armyworm Symposium 2000:37-42), and has a lethal effect on the newly hatched larvae of the oriental armyworms (Wang Zhenying et al., 2005. Evaluation of Indoor Insecticidal Effects of Transgenic Bt Maize on Armyworms, Journal of Plant Protection, 32:153-157).

In addition, further studies have shown that the function of artificially constructed Bt insecticidal fusion proteins is significantly different from the original protein. For example, both Cry1Ab and Cry1Ah have high activity against lepidopteran pests, but the insecticidal activity of the constructed fusion protein Cry1Ab/Cry1Ah has changed significantly, namely the insecticidal activity against *Helicoverpa armigera* has been lost, and the insecticidal activity against corn borer and *Plutella xylostella* has been reduced (Xu Man et al., Cry1Ab/Cry1Ah Hybrid Protein Construction and Functional Study, Biotechnology Bulletin, 2015, 31 (9):91-96).

SUMMARY

In one aspect, the present application provides a method of controlling a population of oriental armyworms, comprising contacting the population of oriental armyworms with a plant, seed, plant cell, progeny plant or plant part having the genome integrated with the gene sequence cry1Ab/cry1AcZM.

The present application also provides a method of killing oriental armyworms, comprising contacting the oriental armyworms with an insecticidally effective amount of a plant, seed, plant cell, progeny plant, or plant part having the genome integrated with the gene sequence cry1Ab/cry1AcZM.

The present application also provides a method of reducing injury to a plant by oriental armyworms, comprising stably integrating an expression vector comprising the gene sequence cry1Ab/cry1AcZM into the genome of the plant.

In particular embodiments, the gene sequence cry1Ab/cry1AcZM in each of the methods described above comprises the nucleotide sequence as set forth in SEQ ID NO: 1, or a nucleotide sequence having at least 90%, at least 95%, at least 98%, or at least 99% sequence identity to the nucleotide sequence as set forth in SEQ ID NO: 1, or a complement thereof.

In particular embodiments, the plant in each of the methods described above is a monocotyledonous plant; optionally, the plant is selected from the group consisting of corn, rice, wheat, oat, barley, highland barley, millet, sorghum and sugarcane.

In another aspect, the present application provides use of a protein expressed by the gene sequence cry1Ab/cry1AcZM in killing oriental armyworms.

The present application also provides use of a protein expressed by the gene sequence cry1Ab/cry1AcZM in the manufacture of an insecticide or biological preparation against oriental armyworms.

In particular embodiments, the gene sequence cry1Ab/cry1AcZM in each of the use described above comprises the nucleotide sequence as set forth in SEQ ID NO: 1, or a nucleotide sequence having at least 90%, at least 95%, at least 98%, or at least 99% sequence identity to the nucleotide sequence as set forth in SEQ ID NO: 1, or a complement thereof.

BRIEF DESCRIPTION OF THE DRAWINGS

FIG. 1 is a photograph of identification of the armyworm resistance using an ex-vivo bioassay, with the missing part of the leaf being the wormholes after being eaten by the armyworms, in which:

A is the transgenic event ZZTM0103; B is the transgenic event ZZM030, C is the positive control Bt11, and D is the negative control Xiang 249.

FIG. 2 is a photograph of identification of the armyworm resistance in the field, with the leaf edge and the missing part of the leaf being the wormholes after being eaten by the armyworms, in which:

A is the transgenic event ZZM030; B is the negative control Xiang 249.

DETAILED DESCRIPTION

The following definitions and methods are provided to better define the application and to guide those of ordinary skill in the art in the practice of the application. Unless otherwise indicated, the terms are to be understood in accordance with conventional usage by one of ordinary skill in the relevant art. All patent documents, academic papers, industry standards, and other publications cited herein are incorporated by reference in their entirety.

As used herein, "plant" encompasses whole plants, plant cells, plant organs, plant protoplasts, plant cell tissue cultures from which plants can regenerate, plant calli, and intact plant cells in plants or plant parts such as embryos, pollens, ovules, seeds, leaves, flowers, branches, fruits, stems, roots, root tips, anthers, and the like.

The gene sequence cry1Ab/cry1AcZM of the present application encodes a protein comprising three functional regions, in which the N-terminal two functional regions are highly homologous to the corresponding portion of Cry1Ab and the C-terminal functional region is highly homologous to the corresponding portion of Cry1Ac.

In particular embodiments, the gene sequence cry1Ab/cry1AcZM referred to herein comprises, or consists of, the nucleotide sequence set forth in SEQ ID NO: 1.

In some embodiments, the gene sequences such as the nucleotide sequence as set forth in SEQ ID NO: 1 of the present application may be altered to produce conservative amino acid substitutions. In certain embodiments, nucleotide sequences of the present application may be replaced according to monocotyledonous codon preference without altering the amino acid sequence, e.g., a codon encoding the same amino acid sequence may be substituted with a codon preferred by a monocotyledonous plant without altering the amino acid sequence encoded by the nucleotide sequence.

In particular, the present application relates to nucleotide sequences which are obtained by further optimizing SEQ ID NO: 1. Further details of the method are described in Murray et al. (1989) Nucleic Acids Res. 17:477-498. Optimized nucleotide sequences can be used to increase the expression of insecticidal protein in a plant such as a monocotyledonous plant, e.g., a gramineous plant, e.g., *Zea mays* L.

In some embodiments, the present application also relates to variants of the sequence as set forth in SEQ ID NO: 1. In general, a variant of a particular nucleic acid sequence will have at least about 90%, 91%, 92%, 93%, 94%, 95%, 96%, 97%, 98%, 99%, 99.5%, or 99.9% or more sequence identity to the particular nucleic acid sequence, or a complement thereof.

Such variant sequences include additions, deletions or substitutions of one or more nucleotides, thereby resulting in the additions, deletions or substitutions of the corresponding amino acid residues. Sequence identity can be determined by sequence alignment procedures known in the art, including hybridization techniques. The nucleotide sequence variants in some embodiments may differ from the sequences of the present application by as little as 1 to 15 nucleotides, as little as 1 to 10 (e.g., 6 to 10), as little as 5, as little as 4, 3, 2, or even 1 nucleotides.

The present inventors have surprisingly found that gene sequence cry1Ab/cry1AcZM has significant resistance to armyworms, in particular oriental armyworms (Mythimna separate (Walker)).

The present application provides a method of controlling a population of oriental armyworms, a method of killing oriental armyworms, and a method of reducing injury to a plant by oriental armyworms.

In one embodiment, the present application provides a method of controlling a population of oriental armyworms, comprising feeding the population of oriental armyworms with a plant, seed, plant cell, progeny plant or plant part having the genome integrated with the gene sequence cry1Ab/cry1AcZM.

In one embodiment, the present application provides a method of killing oriental armyworms comprising feeding the oriental armyworms with an insecticidally effective amount of a plant, seed, plant cell, progeny plant or plant part having the genome integrated with the gene sequence cry1Ab/cry1AcZM.

As used herein, an "effective amount" or "insecticidally effective amount" refers to the amount of an insecticidally active substance or organism in the environment of pests.

In one embodiment, the present application provides a method of reducing injury to a plant by oriental armyworms comprising stably integrating an expression vector comprising the gene sequence cry1Ab/cry1AcZM into the genome of the plant.

In particular embodiments, the gene sequence cry1Ab/cry1AcZM in each of the methods described above comprises the nucleotide sequence as set forth in SEQ ID NO: 1, or a nucleotide sequence having at least 90%, at least 95%, at least 98%, or at least 99% sequence identity to the nucleotide sequence as set forth in SEQ ID NO: 1, or a complement thereof.

In particular embodiments, the plant in each of the methods described above is a monocotyledonous plant; optionally, the plant is selected from the group consisting of corn, rice, wheat, oat, barley, highland barley, millet, sorghum and sugarcane.

In addition, the present application also provides use of a protein expressed by the gene sequence cry1Ab/cry1AcZM in killing oriental armyworms, or use of a protein expressed by the gene sequence cry1Ab/cry1AcZM in the manufacture of an insecticide or biological preparation against oriental armyworms.

In particular embodiments, the gene sequence cry1Ab/cry1AcZM in each of the use described above comprises the nucleotide sequence as set forth in SEQ ID NO: 1, or a nucleotide sequence having at least 90%, at least 95%, at least 98%, or at least 99% sequence identity to the nucleotide sequence as set forth in SEQ ID NO: 1, or a complement thereof.

EXAMPLES

The following examples can illustrate the invention, but are not intended to limit the scope of the invention. Modifications or alternations to the methods, steps or conditions of the present invention are intended to fall within the scope of the present application without departing from the spirit and essence of the invention.

Unless otherwise specified, the examples were performed according to routine experimental conditions, such as the Molecular Cloning Experiment Manual by Sambrook et al. (Sambrook J & Russell D W, Molecular cloning: a laboratory manual, 2001), or as suggested in the manufacturer's specification.

Unless otherwise specified, the chemical reagents used in the examples are conventional commercially available reagents, and the technical means used in the examples are conventional means well known to those skilled in the art.

Materials of maize varieties related in the following examples are all provided by China National Seed Group Corporation, Ltd., in which the maize inbred line Xiang 249 is the female parent of the maize variety Changcheng 799. The Xiang 249 was selectively cultivated from the maize germplasm resources imported from abroad by pedigree self-cross separation and strict selection after 10 generations in 1996.

Example 1: Design and Synthesis of Insect-Resistant Gene

The gene was genetically engineered from 608-amino acid sequence at the N-terminal end of a fused and engineered Cry1Ab and Cry1Ac, and the coding sequence was replaced with codons preferred by plants. After eliminating restriction enzyme digestion sites rich in AT sequence and common restriction enzyme digestion sites resulting in unstable transcription of plants present in the DNA sequence, corrections and eliminations were carried out by replacing the codons; a modified DNA sequence was obtained by adding a termination codon TAA at the 3'end; and a modified sequence as set forth in SEQ ID NO: 1 was identified and chemically synthesized.

A protein encoded by the modified DNA sequence contains three functional regions, where two functional regions at the N-terminal end are highly homologous to the counterpart of Cry1Ab, and the functional region at the C-terminal end is highly homologous to Cry1Ac.

Therefore, the gene in the present application was designated as Cry1Ab/Cry1AcZM.

Example 2. Creation of Transgenic Event Containing the cry1Ab/cry1AcZM Gene

1. Construction of Vector
(1) Construction of Transformation Vector pZHZH25018

Expression optimization was further designed for the upstream and the downstream of the Cry1Ab/Cry1AcZM gene coding region, in order to improve the strength of the gene in the transcriptional level and the efficiency of the protein translation, including adding a fragment of an omega (Ω) sequence consisting of 67 nucleotides and a Kozak sequence consisting of 3 nucleotides (ACC) to the 5' end to enhance the translational efficiency of eukaryotic genes, and a fragment of polyA tail sequence of eukaryotic mRNA to the 3' end to increase transport from the karyon to the cytoplasm, mRNA stability and translational efficiency.

HindIII and PstI digestion sites were added to the 5' end of the synthesized SEQ ID NO: 1, and PmeI digestion site was added to the 3' end. The synthesized sequence was cloned on a Puc57simple vector, designated as pzz01194.

Pzz01194 was digested with the restriction enzyme PstI, and the resulting sticky ends were blunted with T4 DNA polymerase. The vector pzz00002 containing the ubi promoter was digested with the restriction enzymes HindIII+BamHI to obtain a Ubi promoter fragment, and the ends were blunted with T4 DNA polymerase. The Ubi promoter was ligated by blunt end ligation to obtain a vector containing the Ubi-Cry1Ab/Cry1AcZM fragment, designated as pzz01201.

An existing vector containing the Tocs terminator (with EcoRI digestion site at the 5' end, and with PmeI and EcoRI sites at the 3' end) was designated as pzz01131, and the Tocs terminator sequence can be obtained by single digestion of pzz01131 with EcoRI.

Pzz01131 was digested with EcoRI to obtain a Tocs terminator fragment, and the resulting sticky ends were blunted with T4 DNA polymerase.

Figure 1:
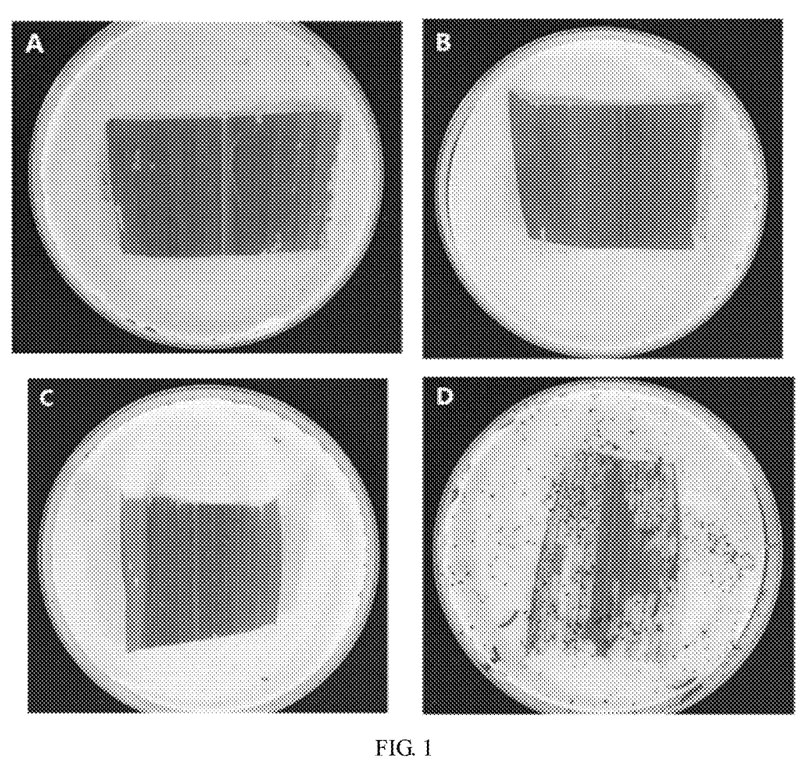

Pzz01201 was digested with PmeI, and the Tocs terminator was ligated by blunt end ligation to obtain a vector containing the fragment Ubi-cry1Ab/cry1AcZM-Tocs, designated as pzz01206 (FIG. 1D).

An element Ubi-egfp-T35spolyA was added to a constructed vector pzz00015 with pCAMBIA3300 (with an element 35s-bar-T35spolyA) as its backbone by double digestion with HindIII+PmeI, Ubi-egfp-T35spolyA can be removed with HindIII+PmeI, and then a new element was added to the sites.

The vector pzz01206 was digested with HindIII+PmeI to obtain the fragment Ubi-cry1Ab/cry1AcZM-Tocs.

The vector pzz00015 was digested with HindIII+PmeI, and Ubi-cry1Ab/cry1AcZM-Tocs was ligated to the digestion sites to obtain an expression vector containing two expression cassettes Ubi-cry1Ab/cry1AcZM-Tocs and 35s-bar-T35spolyA, designated as pZHZH25018.

(2) Construction of Transformation Vector pZHZH35006

HindIII and PstI restriction sites were added to the 5' end of the synthesized cry1Ab/cry1AcZM, and PmeI restriction site was added to the 3' end. The synthesized sequence was cloned into a Puc57 simple vector, which was designated as pZZ01194.

The intermediate vector pZZ00005 containing ubiquitin promoter (with HindIII restriction site at the 5' end and BamHI restriction site at the 3' end) was digested with restriction enzymes HindIII and BamHI, and the resulting sticky ends were blunted with T4 DNA polymerase to obtain an ubiquitin promoter fragment.

PZZ01194 was digested with restriction enzyme PstI, the resulting sticky ends were blunt with T4 DNA polymerase, and the ubiquitin promoter was ligated by blunt end ligation to obtain a vector containing an ubiquitin promoter—cry1Ab/cry1AcZM fragment, designated as pZZ01201.

The intermediate vector pZZ01188 containing nos terminator (with EcoRI restriction site at the 5' end and PmeI and EcoRI restriction sites at the 3' end) was digested with restriction enzyme EcoRI, and the resulting sticky ends were blunted with T4 DNA polymerase to obtain the nos terminator sequence.

pZZ01201 was digested with PmeI and the nos terminator was ligated by blunt end ligation to obtain a vector containing the ubiquitin promoter—cry1Ab/cry1AcZM-nos terminator fragment, designated as pZZ01205.

For the intermediate vector pZZ00015 (containing CaMV 35S promoter-bar-CaMV 35S terminator and ubiquitin promoter—egfp-nos terminator expression element), ubiquitin promoter-egfp-nos terminator was removed by restriction enzymes HindIII and PmeI. The pZZ01205 vector was digested with restriction enzymes HindIII and PmeI to obtain ubiquitin promoter—cry1Ab/cry1AcZM-nos terminator fragment. The two fragments were ligated to obtain an expression vector containing two expression cassettes, ubiquitin promoter—cry1Ab/cry1AcZM-nos terminator and CaMV 35S promoter—bar-CaMV 35S terminator, designated as pZHZH25017.

The intermediate vector pZZ01337 (CaMV 35S promoter—cp4 epspsZM-nos terminator) was digested using restriction enzymes HindIII and BamHI to remove CaMV 35S promoter. The intermediate vector pZZ00033 was digested using restriction enzymes HindIII and BamHI to obtain Ubiquitin4 promoter. The two fragments were ligated to obtain a vector containing the ubiquitin4 promoter—cp4 epspsZM-nos terminator fragment, designated as pZZ01383.

PZZ01383 was digested with restriction enzymes HindII and PmeI to obtain the ubiquitin4 promoter—cp4 epspsZM-nos terminator fragment, and the resulting sticky ends were blunted with T4 DNA polymerase.

PZHZH25017 was digested with restriction enzyme PmeI and ubiquitin4 promoter-cp4 epspsZM-nos terminator was ligated by blunt end ligation to obtain a plant expression vector containing three expression cassettes, ubiquitin promoter—cry1Ab/cry1AcZM-nos terminator, CaMV 35S promoter—bar-CaMV 35S terminator and ubiquitin4 promoter—cp4 epspsZM-nos terminator, designated as pZHZH35006.

2. Genetic Transformation

The above two transformation vectors were transformed into the recipient Xiang 249 using *agrobacterium*-mediated genetic transformation methods, respectively.

The plasmids of the vectors pZHZH25018 and pZHZH35006 were transformed into *agrobacterium* EHA105 by an electroporation method, and were identified prior to use.

Maize inbred line Xiang 249 was self-crossed, and an immature embryo having a length of 1.5 mm was then used for transformation. Immature embryos of about 200 ears were collected in one batch, and placed in an EP tube following by removing of the suspension.

*Agrobacterium* broth containing 200 μM acetosyringone was added, co-cultured for 5 min, and the immature embryos were then transferred onto the co-culture medium and cultured in the dark for 3 days.

After dark culture, the embryos were placed on a callus inducing culture medium. After the formation of calli, the embryos were placed on a selective medium containing 5 mg/L bialaphos for selective culture, and were passaged once every two weeks. After the formation of resistant calli, embryonic calli in good condition were selected and transferred to a differential medium, and cultured under conditions at 26° C. with 3000 Lux illumination intensity for 16 hours every day. Two weeks later, regenerated plantlets appeared.

The regenerated plantlets were transferred to a rooting medium, and were transplanted, after the formation of secondary root, in a small pot with a mixture of nutrient soil and vermiculite (1:3).

3. Determination of Transformation Event
(1) Detection of Positive Transgene

Genomic DNA was extracted from maize using DNAsecure Plant Kit novel plant genomic DNA extraction kit (centrifugal column type) from Tiangen Biochemical Technology Inc. The following reagents at −20° C. were thawed: 10-fold PCR buffer (Takara), deoxynucleotide mixture (10 mM, Sigma), forward primer 5'-CACGCAGATTCCAGCGGTCAA-3', reverse primer 5'-GACGAGGTGAAGGCGTTAGCA-3' and maize leaf DNA template. All the reagents were centrifuged for several seconds after thawing, and placed on ice for later use. A mixture of PCR reaction system was prepared, mixed and centrifuged for several seconds. PCR reaction system (20 μL): 2 μL 10-fold PCR buffer (Takara), 0.5 μL deoxynucleotide mixture (10 mM, Sigma), 0.8 μL forward and reverse primer mixture (5 μM), 0.2 μL r-Taq (5U, Takara), the remaining dd $H_2O$. The mixture was placed into PCR tubes of 200 μL, and 1 μL maize leaf DNA template was added. Different samples were separately marked for differentiation. The PCR reaction tubes were placed in a ABI 9700-type PCR amplification apparatus, and a preset PCR amplification program was selected to start the reaction. The PCR reaction procedure was: pre-denaturation at 94° C. for 2 min; 30 cycles: denaturation at 94° C. for 30 sec, annealing at 58° C. for 30 sec, extension at 72° C. for 30 sec; and finally extension at 72° C. for 5 min.

After completion of PCR, 5 μL of the PCR products were taken for agarose gel electrophoresis detection. A 1.5% agarose gel was prepared and were stained in ethidium bromide (EB) for 10 min after electrophoresis for 25 min and photographed in an ultraviolet gel imaging system.

The materials producing amplification band of 333 bp were transgenic positive plants, and the materials not producing such an amplification band were transgenic negative plants.

(2) Southern Blotting

The probe for detecting cry1Ab/cry1AcZM was synthesized by using the PCR digoxin probe synthesis kit from Roche (Cat. No. 11636090910) with the primers 5'-CACGCAGATTCCAGCGGTCAA-3' and 5'-GACGAGGTGAAGGCGTTAGCA-3'. The amplification system comprised: DNA template 5 μL (50 μg), primers each 0.5 μL, PCR DIG mixture 5 μL, DNA polymerase 0.75 μL, PCR buffer (10-fold) 5 μL, dd$H_2O$ 33.25 μL. The PCR reaction procedure was: pre-denaturation at 94° C. for 5 min; 35 cycles: denaturation at 94° C. for 30 sec, annealing at 55° C. for 30 sec, extension at 72° C. for 45 sec; Finally, extension at 72° C. for 7 min. The amplification effects were detected using 1% agarose gel. The specific amplification product, i.e., the probe for detecting cry1Ab/cry1AcZM, were stored at −20° C.

The total genomic DNA of the leaves of the transgenic maize materials was extracted, and the obtained DNA precipitate was dried and dissolved in non-ionic water. The concentration was determined for later use.

The genomic DNA of the maize was digested with HindIII or KpnI. A 200 μL digestion system was used, which contained 20 μg maize genomic DNA, 20 μl restriction enzyme, 20 μL 10-fold buffer and was supplemented with dd$H_2O$ to 200 μL. The DNA was digested for 16 h, and then 20 μL was taken for electrophoresis to determine whether the enzyme digestion was complete.

The digested products were supplemented with dd$H_2O$ to 400 μl, and 1/10 volume of 3 M sodium acetate solution (pH 5.2) was added, following by adding 4 μL of TaKaRa Dr.

GenTLE Precipitation Carrier and 2.5-fold volumes of absolute ethanol. It was mixed well and centrifuged at 12,000 rpm at 4° C. for 15 min. The precipitate was dissolved in 50 μL ddH$_2$O and 5 μL 6× loading buffer was added.

The DNA was subjected to electrophoresis in a 0.8% gel at 20V for 16 h. Excess lanes and loading wells were cut off and the remaining gels was treated twice with denaturing solution for 15 min each time and shaken gently on a shaker. The gels were treated twice with neutralization buffer for 15 min each time and shaken gently on a shaker. The gels were washed once with ultrapure water. After 20×SSC treatment for 10 min, the DNA was transferred to the membrane for 4 hours or more with the Whatman system.

At the end of the membrane transferring, the membrane was placed on a Whatman 3MM filter paper impregnated with 10×SSC, and allowed to be cross-linked for 3-5 min with an ultraviolet crosslinker. The membrane was simply washed with ddH$_2$O and dried in air. The hybridization and development processes were performed according to the instruction manuals of the digoxin detection kit I from Roche (Cat. No. 11745832910) or the digoxin detection kit II from Roche (Cat. No. 11585614910).

(3) Identification of Corn Borer Resistance

The corn borer resistance of plants in the field was identified by live worm inoculation method at whorl stage of the maize.

The inoculation was carried out when the maize plants were grown to the middle of the whorl stage (7 leaf stage). The test insects were *Ostrinia furnacalis*, in which approximately 60 black-headed eggs were placed in a centrifuge tube and the tube orifice was occluded with defatted cotton. The centrifuge tube was placed in a 28° C. incubator with a humidity of 80%, or placed in a room temperature condition and covered with a wet towel for moisturization. After hatching the eggs, the defatted cotton was removed and the hatched eggs were placed into the heart leaf cluster. Each plant was inoculated with 40-60 worms. At 2-3 weeks after inoculation, the extent of injury to the heart leaf of the plant was investigated, and the injury grade was classified according to the size and the number of the pest holes on the injured leaves, and referred to as the leaf-eating grade. The present application employed a 9 grading standard developed by the International Corn borer Collaboration (Table 1). The leaf-eating grades were investigated on a plant-by-plant basis, with the average of each plant as the leaf-eating grade for the identified line, and their resistance to borer was determined according to the evaluation criteria of Table 1.

After the above steps, the transgenic event ZZTM0103 corresponding to the transformation vector pZHZH25018 and the transgenic event ZZM030 corresponding to the transformation vector pZHZH35006 were screened out, respectively.

Example 3. Identification of Armyworm Resistance of Transgenic Events ZZTM0103 and ZZM030

The commercial transgenic maize variety Btl1 from Syngenta, which contains the Cry1Ab gene and has been reported to be resistant to armyworms, was used as a positive control; The recipient maize Xiang 249 used for constructing the transgenic event was used as a negative control; The ex-vivo bioassay was performed on ZZTM0103, ZZM030, Bt11 and Xiang 249 for its resistance to armyworm; The test armyworm was Mythimna separate (Walker).

Specific identification methods were as follows: Fresh maize plants grown to 3-4 and 8-10 leaf stages, respectively, were brought into a room, young heart leaves were taken and placed in a culture dish, and 10 1-day-old insects were inoculated; Each dish was subject to one treatment, and each treatment was repeated three times; The culture dishes were incubated in an artificial climate chamber at 28±1° C. with photoperiod of 14:10 h (L:D), and relative humidity of 70-80%. After 3 days, the number of live larvae was counted and the survival rate of the larvae was calculated.

The survival rates of armyworms on different maize varieties were analyzed by multiple comparison with the significant level of 0.05. The survival rate was subjected to a square and inverse sine transformation prior to statistical analysis, and the difference significance between the treatments were compared. According to the difference significance of the survival rate of the larvae fed on the transgenic maize and the control maize, their armyworm resistance was qualitatively determined with reference to Table 2.

TABLE 2

Evaluation criteria of *Mythimna Separate* Ex-vivo bioassay

| Resistance level | Larval survival (Y) % |
| --- | --- |
| High Resistance | Y ≤ 10 |
| Resistance | 10 < Y ≤ 20 |
| Moderate Resistance | 20 < Y ≤ 45 |

TABLE 1

Field evaluation criteria for maize bore resistance

| Shape of injured heart leaf | | Leaf-eating grade | Injury to stems (hole/plant *) | Borer resistance type ** |
| --- | --- | --- | --- | --- |
| Needle-like or pinhole sized wormhole | Several leaves, rare, dispersed | 1 | 0-2 | HR |
| | Several leaves, medium number | 2 | 0-2 | HR |
| | A few leaves, a large number | 3 | 0-2 | R |
| Mung bean-sized wormhole, some leaves exhibiting short striped-holes | Several leaves, rare, dispersed | 4 | 0-2 | R |
| | Few leaves, medium number | 5 | 3-5 | MR |
| | Some leaves, a large number | 6 | 3-5 | MR |
| Wormhole larger than mung bean, leaves having rows of holes, long-striped-holes, with withered center | Few leaves, rare, dispersed | 7 | 3-5 | S |
| | Some leaves, medium number | 8 | 3-5 | S |
| | Most leaves, a large number | 9 | >6 | HS |

Note:
* 1 hole in tunnel 2.5 cm when assessing injury to stems.
** HR: High resistance; R: Resistance; MR: Moderate resistance; S: Sensitivity; HS: High Sensitivity TABLE 2-continued Evaluation criteria of *Mythimna Separate* Ex-vivo bioassay

| Resistance level | Larval survival (Y) % |
|---|---|
| Sensitivity | 45 < Y ≤ 60 |
| High Sensitivity | 60 < Y, close to control or the same |

The identification results were shown in Table 3 and FIG. 1. In FIG. 1, A is the transgenic event ZZTM0103, B is the transgenic event ZZM030, C is the positive control Btl1, and D is the negative control Xiang 249; The missing parts of the leaf is the wormholes after being eaten by the armyworms.

TABLE 3

Ex-vivo Bioassay Results of Different Maize Materials

| Transgenic event | Survival rate (%) | Resistance level |
|---|---|---|
| ZZTM0103 | 29.41 | Moderate resistance |
| ZZM030 | 22.55 | Moderate resistance |
| Btl1 | 2.94 | High resistance |
| Xiang 249 | 70.00 | High Sensitivity |

Example 4. Identification of Armyworm Resistance of Transgenic Events ZZTM0103 and ZZM030

The commercial transgenic maize variety Btl1 from Syngenta, which contains the Cry1Ab gene and has been reported to be resistant to armyworms, was used as a positive control; The recipient maize Xiang 249 used for constructing the transgenic event and the conventional maize, on which various generations of armyworms (studied by Migratory Pest Research Group, Plant Protection Research Institute, Chinese Academy of Agricultural Sciences) fed, were used as a negative control; The ex-vivo bioassay was performed on the transformation events ZZTM0103 and ZZM030 for their resistance to armyworms; The test armyworm was Mythimna separate (Walker).

Specific identification methods were as follows: Fresh maize leaves at the 3-4 and 8-10 leaf stages were selected as food for the test armyworm; All the maize leaves were sterilized by being soaked in 0.1% sodium hypochlorite solution for 3 min and then washed with distilled water and air-dried; The whole maize plant was placed in a canned bottle of 750 ml, and 40 newly hatched larvae were placed therein. Each treatment was repeated three times; The bottles were placed in an artificial climate chamber at a temperature of (24±1°) C with humidity of (70±5)%, and photoperiod of 14 L:10 D; Fresh maize plants which had received corresponding treatments were replaced every 2 days and larvae were examined for death on days 3, 6, and 9 after the start of the test, respectively.

The survival data of larvae receiving different treatments on days 3, 6, and 9 were sorted by Excel, and variance analysis was performed for the survival rates of larvae receiving different treatments by using SPSS software (SPSS 16.0) of SPSS Inc. of the United States of America. If the difference was significant, and then multiple comparisons were made using Tukey's HSD. Survival data were subjected to a square and inverse sine transformation prior to statistical analysis.

Table 4 shows the effect of different materials at 3-4 leaf stage on the survival rate of freshly hatched armyworms. The data in the Table are mean standard error. The same letter in the same column indicates that there is no significant difference at the P<0.05 level by the Tukey's HSD test. The survival rates of the larvae of the armyworms on the conventional maize plantlets were more than 95% after treatment and on days 3, 6 and 9, indicating that the insects used in the experiment were healthy and the experiment was feasible. The survival rates of the newly hatched larvae were significantly affected by the different materials at 3-4 leaf stage. The survival rates of the larvae on each material on the third day were higher, and except that the survival rate of the Btl1 larvae was significantly lower than that of other materials (P<0.05), there was no significant difference between other treatments (P>0.05). On day 6, the difference in larval survival was even more significant among the treatments, and in particular the Btl1 larval survival decreased significantly, only to 31.7%, the resistance level of which was moderate according to the evaluation criteria of Table 5. On day 9, the difference of larval survival among treatments was further increased.

TABLE 4

Effect of Different Materials at 3-4 Leaf Stage on Survival Rate of Newly hatched Armyworms

| Transgenic event | Day 3 survival | Day 6 survival | Day 9 survival |
|---|---|---|---|
| ZZTM0103 | (95.0 ± 1.14) ab | (73.3 ± 6.01) bc | (55.83 ± 3.33) b |
| ZZM030 | (98.33 ± 0.83) a | (75.0 ± 5.00) b | (55.83 ± 3.60) b |
| Btl1 | (82.5 ± 3.81) b | (31.7 ± 1.67) d | (16.17 ± 2.23) c |
| Xiang 249 | (100 ± 0.00) a | (98.3 ± 0.83) a | (90.83 ± 1.72) a |
| Conventional maize | (98.33 ± 1.67) a | (97.5 ± 1.44) a | (95.83 ± 2.22) a |

Table 5 shows the effect of different materials at 8-10 leaf stage on the survival rate of freshly hatched armyworms. The data in the Table are mean standard error. The same letter in the same column indicates that there is no significant difference at the P<0.05 level by the Tukey's HSD test. The survival rate of Btl1 larval was significantly lower than that of Xiang 249 and conventional maize plantlets on 3 day after the test. The difference among larval survival rates at day 6 after treatment was significantly increased: the survival rates of larvae on ZZTM0103 and ZZM030 were lower than 45%, showing a moderate resistance; Xiang 249 and conventional maize plantlets showed high sensitivity. On 9 days after treatment, Xiang 249 and conventional maize plantlets showed high sensitivity in terms of the larval survival rate and were significantly higher than other materials. ZZM030 showed high resistance; and ZZTM0103 showed resistance. However, there was no significant difference between the two transgenic events.

TABLE 5

Effect of Different Materials at 8-10 Leaf Stage on Survival Rate of Newly hatched Armyworms

| Transgenic event | Day 3 survival | Day 6 survival | Day 9 survival |
|---|---|---|---|
| ZZTM0103 | (80.83 ± 6.01) ab | (35.00 ± 4.33) c | (20.00 ± 5.20) c |
| ZZM030 | (70.00 ± 9.46) ab | (21.67 ± 3.63) cd | (8.33 ± 0.83) c |
| Bt11 | (57.50 ± 1.64) b | (20.83 ± 6.51) cd | (6.67 ± 3.63) c |
| Xiang 249 | (99.17 ± 0.83) a | (98.33 ± 1.67) a | (93.33 ± 3.00) a |
| Conventional maize | (99.17 ± 0.83) a | (98.33 ± 0.83) a | (91.67 ± 0.83) a |

Example 5. Resistance Identification of Transgenic Event ZZM030 to Armyworm in the Field Three experimental locations were set up in Gong Zhong ling (Jilin), Yin ma Quan (Jinan) and Jing Hong (Yunnan) to identify the resistance of ZZM030 in the field to armyworms in the form of living insects. Xiang 249 was used as a control and the test armyworms were Mythimna separate (Walker). The inoculation method was: 4-6 leaf stage, 40 plants per location, 40 newly hatched larvae per plant; Inoculation was performed twice with 3 day interval; On day 14 after the last inoculation, leaf-eating grades of plants inoculated by larvae in each location were investigated and the resistance levels of the materials at whorl stage were evaluated according to the criteria. The grading criteria and the resistance level determination criteria were performed in accordance with the provisions of the Ministry of Agriculture Publication No. 953-10.1-2007.

Figure 2:
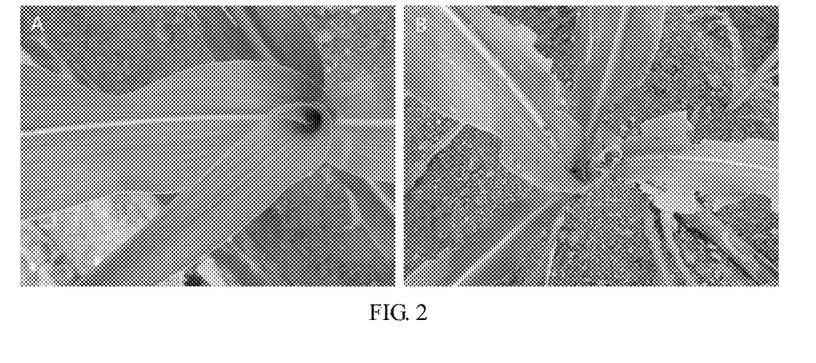

The identification results were shown in Table 6 and FIG. 2. In Table 6, the values are expressed as the mean±standard deviation of 3 replicates, and the lowercase letters in the same column indicate significant differences between different materials at the same location (P<0.01).

In FIG. 2, A is the transgenic event ZZM030 and B is the negative control recipient maize Xiang 249. The edge of the leaf and the missing part of the leaf are the wormholes after being eaten by the armyworms. In the test location of Gong Zhong ling, the ZZM030 had an average leaf-eating grade of 1.2 and high resistance, and the negative control recipient maize Xiang 249 had an average leaf-eating grade of 5.8 and moderate resistance; In the test location of Jinan, the ZZM030 had an average leaf-eating grade of 2.7, and resistance, and the negative control recipient maize Xiang 249 had an average leaf-eating grade of 5.4, and moderate resistance. In the test location of Jing Hong, the ZZM030 had an average leaf-eating grade of 1.5 and high resistance, and the negative control recipient maize Xiang 249 had an average leaf-eating grade of 9.0 and high resistance. The resistance of the transformation event ZZM030 to armyworms was significantly different from that of the negative control (the recipient maize Xiang 249) at three test locations, indicating that the transformation event ZZM030 at the 4-6 leaf stage had better resistance to armyworms under field conditions.

TABLE 6

Identification of Resistance of Different Materials in the Field

| Test location | Material name | Average leaf-eating grade | Resistance type |
|---|---|---|---|
| Gong Zhu Ling | ZZM030 | 1.2 ± 0.2 B | High resistance (HR) |
| | Xiang 249 | 5.8 ± 0.4 A | Moderate resistance (MR) |
| Yin ma Quan | ZZM030 | 2.7 ± 0.2 C | Resistance (R) |
| | Xiang 249 | 5.4 ± 0.2 B | Moderate resistance (MR) |
| Jing Hong | ZZM030 | 1.5 ± 0.3 B | High resistance (HR) |
| | Xiang 249 | 9.0 ± 0.0 A | High sensitivity (HS) |

The foregoing descriptions are merely preferred embodiments of the present invention. It should be noted that those of ordinary skill in the art may make several modifications and variations without departing from the technical principles of the present invention, which are also considered falling into the scope of the present invention.

What is claimed is:

1. A method of controlling a population of oriental armyworms, comprising:
   integrating into the genome of a plant, seed, plant cell, progeny plant or plant part the gene sequence cry1Ab/cry1AcZM comprising the nucleotide sequence as set forth in SEQ ID NO: 1; and
   (ii) selecting a transgenic plant derived from (i) that exhibits resistance to oriental armyworms, thereby controlling the population of oriental armyworms on the transgenic plant.

2. A method of killing oriental armyworms, comprising:
   (i) integrating into the genome a plant, seed, plant cell, progeny plant, or plant part, the gene sequence cry1Ab/cry1AcZM comprising the nucleotide sequence asset forth in SEQ ID NO: 1; and
   (ii) selecting a transgenic plant derived from (i) that exhibits resistance to oriental armyworms, thereby killing oriental armyworms on the transgenic plant.

3. A method of reducing injury to a plant by oriental armyworms, comprising:
(i) stably integrating an expression vector comprising the gene sequence cry1Ab/cry1AcZM into the genome of the plant, the gene sequence cry1Ab/cry1AcZM comprising the nucleotide sequence as set forth in SEQ ID NO: 1; and
(ii) selecting a transgenic plant derived from (i) that exhibits resistance to oriental armyworms, thereby reducing injury to the transgenic plant by oriental armyworms.

4. The method of claim 1, wherein the plant is a monocotyledonous plant; optionally, the plant is selected from the group consisting of corn, rice, wheat, oat, barley, highland barley, millet, sorghum and sugarcane.

5. The method of claim 2, wherein the plant is a monocotyledonous plant; optionally, the plant is selected from the group consisting of corn, rice, wheat, oat, barley, highland barley, millet, sorghum and sugarcane.

6. The method of claim 3, wherein the plant is a monocotyledonous plant; optionally, the plant is selected from the group consisting of corn, rice, wheat, oat, barley, highland barley, millet, sorghum and sugarcane.

7. The method of claim 1, wherein the selecting for resistance to oriental armyworms comprises at least one of:
(i) selecting for a decreased armyworm larvae survival rate in an ex-vivo bioassay using young heart leaves from the transgenic plant;
(ii) selecting for a decreased number of visible wormholes in leaves from the transgenic plant caused by oriental armyworms;
(iii) selecting for a reduced survival rate of newly hatched armyworms when the transgenic plant is the only food source provided, wherein the survival rate is measured at the 3-4 leaf stage or the 8-10 leaf stage; and
(iv) selecting for a lower average leaf-eating grade of the transgenic plant in the field.

8. The method of claim 2, wherein the selecting for resistance to oriental armyworms comprises at least one of:
(i) selecting for a decreased armyworm larvae survival rate in an ex-vivo bioassay using young heart leaves from the transgenic plant;
(ii) selecting for a decreased number of visible wormholes in leaves from the transgenic plant caused by oriental armyworms;
(iii) selecting for a reduced survival rate of newly hatched armyworms when the transgenic plant is the only food source provided, wherein the survival rate is measured at the 3-4 leaf stage or the 8-10 leaf stage; and
(iv) selecting for a lower average leaf-eating grade of the transgenic plant in the field.

9. The method of claim 3, wherein the selecting for resistance to oriental armyworms comprises at least one of:
(i) selecting for a decreased armyworm larvae survival rate in an ex-vivo bioassay using young heart leaves from the transgenic plant;
(ii) selecting for a decreased number of visible wormholes in leaves from the transgenic plant caused by oriental armyworms;
(iii) selecting for a reduced survival rate of newly hatched armyworms when the transgenic plant is the only food source provided, wherein the survival rate is measured at the 3-4 leaf stage or the 8-10 leaf stage; and
(iv) selecting for a lower average leaf-eating grade of the transgenic plant in the field.

* * * * *

SEQUENCE LISTING

<160> NUMBER OF SEQ ID NOS: 1

<210> SEQ ID NO 1
<211> LENGTH: 1824
<212> TYPE: DNA
<213> ORGANISM: Artificial Sequence
<220> FEATURE:

<223> OTHER INFORMATION: Synthetic

<400> SEQUENCE: 1

```
atggattgcc ggccctacaa ctgcctgtcg aaccctgagg tggaggtcct gggcggcgag      60
cggattgaga ctggctacac accgattgac atctcactct ccctgaccca gttcctcctg     120
tcggagttcg tgccaggcgc tgggttcgtt ctcggcctgg tggatatcat ttggggcatc     180
ttcgggccaa gccagtggga cgctttcctg gtccagatcg agcagctcat taatcagagg     240
atcgaggagt tcgcgcggaa ccaggctatt agccgcctcg agggcctgtc gaacctctac     300
cagatctacg ccgagagctt cagggagtgg gaggctgatc cgacgaaccc cgccctgagg     360
gaggagatgc ggattcagtt caatgacatg aactccgctc tgaccacggc tatcccactc     420
ttcgcggtgc agaattacca ggtcccactc ctgagcgtct acgtgcaggc tgcgaacctc     480
cacctgtctg tgctgcgcga tgtttcagtg ttcggccaga cctgggggtt cgacgctgct     540
acgattaatt ccaggtacaa cgatctgaca cggctcatcg gcaattacac tgaccatgcc     600
gttcggtggt acaacaccgg cctcgagagg gtgtggggc cagactccag ggattggatt     660
aggtacaacc agttccgcag ggagctcaca ctgactgtcc tggacatcgt ttccctcttc     720
ccaaactacg atagccggac ctaccctatt cgcacggtgt cccagctgac aagggagatc     780
tacactaatc cagtcctcga gaacttcgac ggctcttttcc gcgggtcagc tcagggcatt     840
gaggggtcca tcaggagccc tcacctgatg gatatcctca actcaatcac catctacacg     900
gacgctcacc gcggcgagta ctactggtcc gggcatcaga tcatggcttc cccagtcggc     960
ttcagcgggc cagagttcac cttcccactg tacggcacga tggggaacgc tgctccacag    1020
cagaggatcg ttgctcagct cggccagggg gtgtaccgca cactgtccag cactctctac    1080
cggcgcccgt tcaacatcgg cattaacaat cagcagctga gcgtgctcga cggcacagag    1140
ttcgcctacg ggacttcgtc taacctgccc tcggcggtct acaggaagtc gggcaccgtt    1200
gactctctcg atgagatccc gccccagaac aataacgtcc cacctcgcca gggcttctcg    1260
cacaggctgt cgcatgtttc tatgttccgg tcaggcttct ccaactcatc cgtctccatc    1320
attagggccc cgatgttctc atggatccac cggtccgcgg agttcaataa catcattgct    1380
agcgattcga tcacgcagat tccagcggtc aagggcaatt tcctcttcaa cgggagcgtt    1440
atctcgggcc ctgggttcac aggcggggac ctggtgaggc tcaatagctc gggcaataac    1500
atccagaaca ggcggtacat tgaggtccca atccacttcc cttctacctc aacgcgctac    1560
agggtccggg ttcgctacgc gtccgtgaca ccaattcatc tgaatgtcaa ctggggcaat    1620
tcttcaatct tctcgaacac tgtgcctgcc acagcgactt ctctggacaa tctccagtcc    1680
agcgatttcg gctacttcga gtctgctaac gccttcacct cgtctctcgg caatatcgtg    1740
ggggtccgca acttcagcgg cacggctggc gttattattg ataggttcga gttcatccct    1800
gttactgcta ccctggaggc tgag                                          1824
```